United States Patent [19]

Bushman

[11] Patent Number: 5,404,225
[45] Date of Patent: * Apr. 4, 1995

[54] OBJECT DETECTOR

[75] Inventor: Boyd B. Bushman, Lewisville, Tex.

[73] Assignee: Lockheed Corporation, Fort Worth, Tex.

[ * ] Notice: The portion of the term of this patent subsequent to Nov. 23, 2010 has been disclaimed.

[21] Appl. No.: 93,223

[22] Filed: Jul. 14, 1993

Related U.S. Application Data

[63] Continuation-in-part of Ser. No. 947,281, Sep. 17, 1992, and a continuation-in-part of Ser. No. 851,281, Feb. 7, 1992, Pat. No. 5,264,916.

[51] Int. Cl.$^6$ .............................. G01J 4/00; G02F 1/01
[52] U.S. Cl. ...................................... 356/364; 359/371; 359/407; 359/501; 250/330; 250/342
[58] Field of Search ............... 356/364, 366, 367, 368; 359/371, 386, 407, 483, 485, 501; 250/330, 342

[56] References Cited

U.S. PATENT DOCUMENTS

| | | |
|---|---|---|
| 2,165,974 | 7/1939 | Land . |
| 3,192,825 | 7/1965 | Courtney-Pratt et al. . |
| 3,633,212 | 1/1972 | Cooper . |
| 4,515,443 | 5/1985 | Bly . |
| 4,763,361 | 8/1988 | Honeycutt et al. . |
| 5,138,162 | 8/1992 | Hacskaylo . |
| 5,264,916 | 11/1993 | Bushman .................. 356/364 |

OTHER PUBLICATIONS

"Polarization Optics Catalog & Handbook", 1992 (pp. 10–15).
"NASA Tech Briefs", May, 1993, vol. 17, No. 5 (p. 52).
"Technical Support Package", Device for Perception of Polarization, MSC-21915.
S.N. 07/863,883, filed Apr. 6, 1992, Victor S. Whitehead and Kinsel Coulson.

*Primary Examiner*—Mark Hellner
*Attorney, Agent, or Firm*—James E. Bradley

[57] ABSTRACT

A device will assist in detecting man-made objects by using a liquid crystal retarder and a stationary polarizer. The liquid crystal retarder shifts impinging light 90 degrees between a nonrotated and a rotated mode. In the nonrotated mode, the retarder is essentially transparent, with the light passing through the retarder and through the polarizer. In the rotated mode, the impinging light will be rotated 90 degrees. An observer viewing the light passing through the polarizer will detect a difference or a flashing, with the rate depending upon the speed of oscillation between the rotated and nonrotated modes. The system can be employed with visible light optical systems such as binoculars, or with an infrared detector or video camera.

26 Claims, 2 Drawing Sheets

OBJECT DETECTOR

CROSS REFERENCE TO RELATED APPLICATION

This application is a continuation in part of Ser. No. 07/947,281, filed Sep. 17, 1992, "Object Discriminator", Boyd B. Bushman, and continuation in part of application Ser. No. 07/851,281, filed Feb. 7, 1992, now U.S. Pat. No. 5,264,916 "Object Detection System", Boyd B. Bushman. Also, an application by the same inventor entitled "Object Locator", attorney docket P-33-9310, is being filed simultaneously with this application.

BACKGROUND OF INVENTION

1. Field of Invention

This invention relates in general to detecting objects by detecting light reflections from an object, and in particular, to a system that utilizes a polarizer and a liquid crystal retarder for viewing light reflected from an object when the retarder oscillates between two different angles of polarization.

2. Description of Prior Art

This invention deals with a method of detecting objects, such as military targets. The targets may be trucks, tanks, artillery, aircraft, command centers and other systems. These objects may be protected by camouflage, foliage, or may be painted with a amouflage paint.

Presently, objects are detected visually through binoculars. Objects may also be detected by other techniques such as radar, infrared and night vision amplification systems. The prior systems do not always adequately detect an object, particularly objects that are camouflaged.

There are needs for detecting objects other than in military applications also. For example, the highest reason for helicopter crashes is due to collisions with high tension electric wires, guide wires or other suspending cables. These cables are difficult to see by the pilot. At present, there is no particular means for detecting such cables other than visually.

SUMMARY OF INVENTION

In this invention, a polarizer filter is employed for detecting objects. The polarizer is of a conventional type, having a large number of very finely spaced parallel lines. Military vehicles have high concentrations of materials such as glass, plastic, paints, rubbers, etc. When such materials are viewed through a polarizer which is polarizing at one angle, they will have one appearance. When polarizing at another angle, 90 degrees from the first angle, the reflected light will be quite different in intensity from the first view. Consequently, alternating the polarization from one angle to the other angle rapidly will cause the reflection from objects such as military vehicles to appear to flash as the polarization angle alternates.

Most natural backgrounds do not show the polarizing contrast between angles of polarization. Consequently, as the polarization angle alternates, the background surrounding the military vehicle gives a steady signal which is not highlighted to the eye. The fluctuating targets stand out, giving away their location. Neither camouflage nor moderate foliage stops the systems from highlighting military targets because adequate flashing still can be observed. This system is also applicable to detecting high tension electrical wires.

In the embodiments in this invention, the alternating angles of polarization are produced by a liquid crystal retarder. The liquid crystal retarder is a conventional optical device that has two transparent plates with a liquid crystal substance located between. An annular housing surrounds the assembled plates and liquid crystal substance. When the plates are energized with a selected voltage level, the electrical field will cause light entering the retarder to rotate. In the embodiments herein, the voltage is such that the light will rotate 90 degrees from the angle at which it is entering. A polarizer filter follows the liquid crystal retarder, the polarizer filter being mounted stationarily to the apparatus.

An electrical circuit will apply at a selected rate alternating voltages, one of which may be zero, causing the retarder to oscillate. The circuitry is conventional, and can be varied in frequency to speed up or slow down the cycling of the liquid crystal retarder. Viewing man-made objects through the polarizer and retarder will cause them to appear to flash as the retarder is cycled between the two angles.

In one embodiment, the liquid crystal retarder and circuitry are mounted at each optical array of a set of binoculars. The observer using the binoculars will see flashes of smooth man-made objects as the retarder cycles, while the background remains uniform. The flashes pinpoint military targets to an observer. In another embodiment, the retarder and polarizer are mounted in the optical path of an infrared camera. A monitor will display the images observed. This system can be utilized at night as well as day.

In another embodiment, a video camera is employed. A liquid crystal retarder and stationary polarizer are mounted in the optical path of the video camera. The video camera is conventional, having a scanning device which provides signals to a video processor. The video processor provides electrical signals to a monitor or display. An observer of the monitor will see flashes of smooth man-made objects as the liquid crystal retarder operates.

Also, in this invention, a notch electronic filter may be located between the signal processor and the display of the video camera. The notch filter passes a lower level frequency needed for video camera monitor operation and also can be varied to pass only signals above a selected frequency far higher than the lower level. The high cut on frequency may be selected to be in the range from 100 KHZ to two MHZ. The notch filter reduces the background viewed by the monitor.

DETAILED DESCRIPTION OF INVENTION

Figure 1:
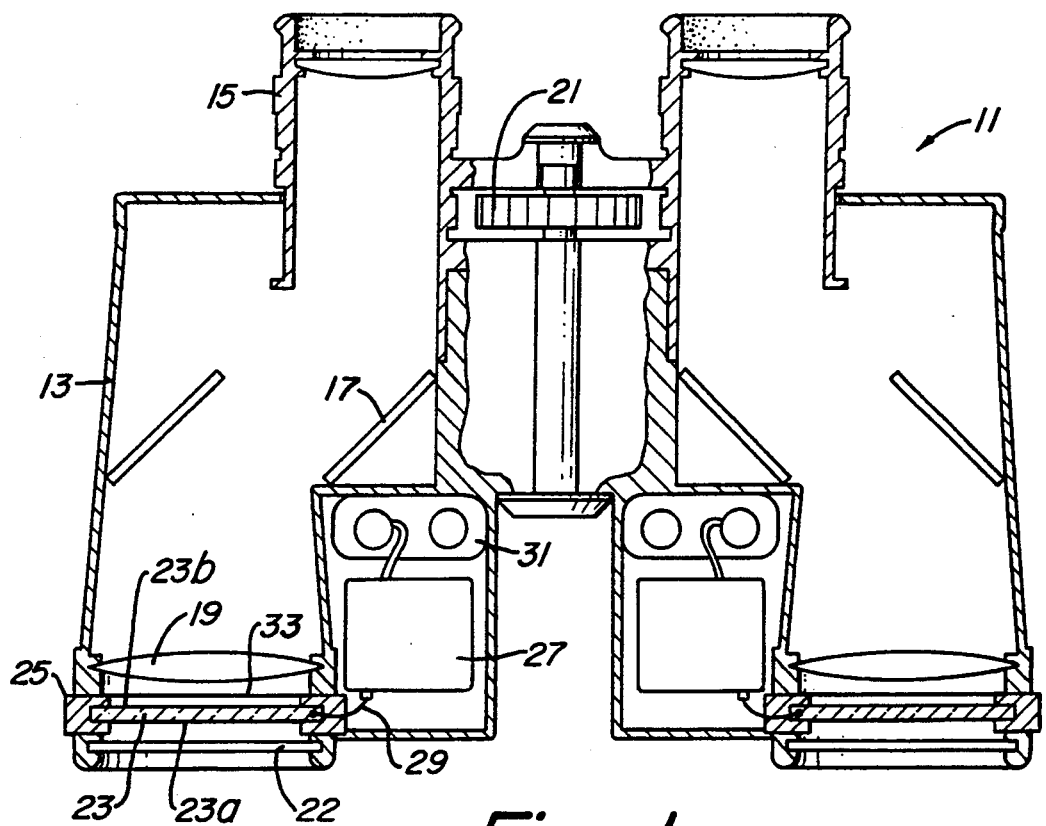
FIG. 1 illustrates schematically a sectional view of a pair of binoculars having a polarizer and liquid crystal retarder constructed in accordance with this invention.

Referring to FIG. 1, binoculars 11 have a basic conventional design, and are normally much more detailed than shown. Binoculars 11 have a housing 13. Two eyepieces 15 mounted telescopically to housing 13. Mirrors 17 located within housing 13 deflect light passing inward through a lens 19. A focal adjuster 21 will vary the distance between eyepiece 15 and lens 19 for focusing. A transparent shield 22 in each image path protects the lens 19. Normally, the optical array will include other lenses as well.

A liquid crystal retarder 23 is mounted in the path of lens 19. Liquid crystal retarder 23 has transparent forward and rearward plates 23a, 23b, with a liquid crystal substance sandwiched between. The thickness is exaggerated in FIG. 1. A metal ring or housing 25 surrounds and supports retarder plates 23a, 23b. An electronic circuit 27 is connected by a wire 29 to housing 25 of retarder 23. Circuit 29 will produce a waveform that oscillates between two voltages, one of which may be zero. A switch and control (not shown) will allow the frequency of the waveform to be changed. The waveform produces an oscillating electrical field on the substance between plates 23a, 23b.

Retarder 23 has a rotated mode when one of the voltages is applied, in which it will rotate light that is passing through plates 23a, 23b and the liquid crystal substance. In the nonrotated mode at the other voltage level, the light passes through substantially without deflection or any diminution in intensity. The circuit 27 will cause the rotation to be 90 degrees from one mode to the other. A battery 31 supplies power for circuit 27.

A conventional stationary linear polarizer 33 locates rearward of retarder 23. Polarizer 33 has a number of finely divided lines (not shown) which may be scribed or otherwise etched on the surface. Also, polarizer 33 may be formed by a chemical coating which aligns the molecules in parallel lines. Polarizer cubes are also commercially available. The lines within the polarizer 33 are extremely closely spaced and are parallel to each other. The distance between the lines of the polarizer 33 is less than the wavelength of light for which the polarizer is designed.

Polarizers, such as polarizer 33, have been known in the past. A polarizer will remove the glare from light reflected from certain objects when the lines are oriented at one angle, such as horizontally. This occurs as a result of some of the light waves striking the reflected object being unable to pass through the finely separated lines. If the polarizer is then rotated 90 degrees, then the glare will return, as reflected light waves will be able to pass through the polarizer. The lines of the polarizer will be invisible in either event to an observer. Rotating a polarizer will thus result in images of certain objects flashing in proportion to the speed of rotation.

In this invention, the polarizer 33 is not rotating, rather it will be held stationary with binoculars 11. Instead, the retarder 23, as it alternately cycles electronically, will cause the same effect as if the polarizer 33 were rotating itself. An observer observing the light passing through the oscillating retarder 23 and stationary polarizer 33 will observe flashing if the object being observed is of the type that is manmade, having a smooth appearance. For visual determinations of the flash, the retarder is preferably cycled approximately five to twelve times per second. Regardless of the orientation of polarizer 33, whether its lines are vertical or horizontal, flashing will appear as the retarder 23 rotates the impinging light.

Liquid crystal retarder 23, including its circuit 27, is a commercially available device. It is known as a variable retarder because the frequency can be varied as well as the degree of retardation. One such device is manufactured by Meadowlark Optics, 7460 Weld County Road 1, Longmont, Colo. 80504, under the designation Model B 1020.

In the operation of the embodiment of FIG. 1, the observer will place his eyes next to the eyepieces 15 and scan a selected terrain. If the observer is not actuating retarder 23, then retarder 23 will perform no function, allowing light to pass without deflection. Approximately 97% of the light will transmit without diminution through liquid crystal retarder 23. Depending upon the orientation of polarizer 33, some glare may be reduced because polarizer 33 will polarize the light which it receives.

The user then may begin cycling retarder 23 by controlling circuit 27. The oscillating voltages supplied to retarder 23 will*p404Xcanetearer 23 to alternately twist or rotate light impinging on retarder 23. When combined with polarizer 23, the light will shift 90 degrees, such as between horizontal and vertical polariation. Light reflected from man-made ojects will appear to flash as the retarder 23 cycles. Most natural objects in the background will not flash, because the reflected light from natural surfaces usually does not produce a strong polarizing contrast. The flashing will pinpoint military targets to the viewer.

Three-dimensional man-made objects normally have horizontal and vertical surfaces which reflect. Consequently, polarizer 33 will display flashing whether it is oriented vertically or horizontally on binoculars 11. For example, if polarizer 33 is stationarily mounted with its lines horizontally oriented as the binoculars 11 are held normally, when retarder 23 is in a nonrotated mode, light from man-made horizontal reflecting surfaces will be polarized. When retarder 23 is in its rotated mode, light reflected from the horizontal surfaces of a man-made object will not be polarized because of the orientation of polarizer 33. In that manner, the horizontal surfaces will appear to flash.

Similarly, the vertical surfaces of a man-made object reflect more intensely through a horizontally oriented polarizer when the retarder 23 was in the nonrotated mode. When retarder 23 is in a nonrotated mode and polarizer 33 is mounted horizontally, vertical surfaces will not be polarized by polarizer 33. When retarder 23 is shifted to the rotated position, polarizer 33 will polarize the light reflected from a vertical surface if it is mounted horizontally. An observer thus viewing a man-made object with horizontal and vertical surfaces will see alternating flashing of the horizontal and vertical surfaces due to the operation of the retarder 23.

Figure 3:
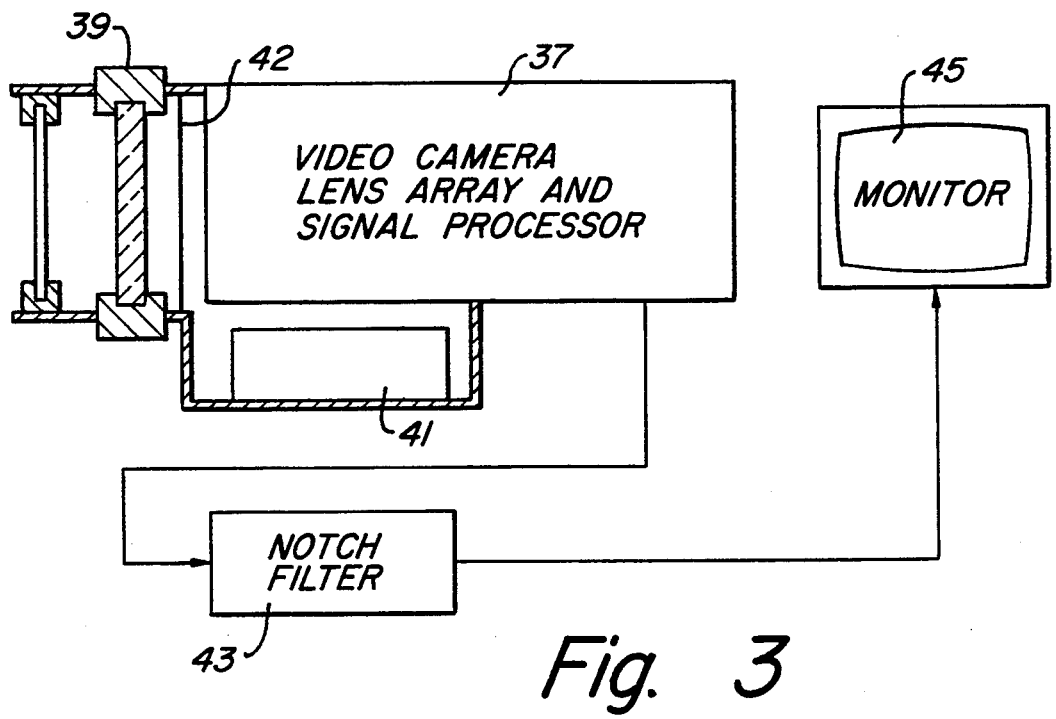
FIG. 3 is a schematic view of a video camera having a polarizer and liquid crystal retarder mounted to it in accordance with this invention.

A video camera 37 is employed with the embodiment of FIG. 3. Video camera 37 is of a conventional type. Objects viewed by video camera 37 are converted into electrical signals which are displayed electronically. Video camera 37 will produce flashing or pulsing images reflected from man-made objects having smooth surfaces. Video camera 37 has a lens array which defines an image path for light being received. A conventional signal processor in video camera 37 will produce analog electrical signals proportional to the objects viewed. In a conventional camera system, these signals may be recorded on videotape or film. Also, the signals may pass to a television monitor or display for viewing.

Liquid crystal retarder 39 is mounted to the video camera 37 in the image path. An electronic circuit 41 cycles liquid crystal retarder 39 in the same manner as liquid crystal retarder 23 of the first embodiment. A polarizer 42 mounts stationarily to video camera 37 rearward of retarder 39. The oscillation speed may be the same as in the embodiment of FIG. 1, or it may be much faster. If faster than about 12 cycles per second, electronic circuitry (not shown) must be employed to detect objects that provide flashing images due to the different angles of polarization.

While the flashing may be observed directly on a monitor if the rate is low enough, in this instance, preferably electrical signals from video camera 37 first pass through a notch electronic filter 43 before being displayed on monitor 45. Filter 43 is of a notch type, which blocks frequencies within a range. Filter 43 will pass signals below a selected level necessary for television monitor operations, such as the sweep. This lower level is normally 17,750 Hz. Filter 43 will block, filter or delete those between 17,750 Hz and a selected high cut-on level, and pass those above, all of which processes are referred to herein as "filtering". This high cut-on or selected frequency is selected to be high enough to eliminate much of the background objects which reflect light that is not affected by retarder 39 and polarizer 42 when operating. This frequency is much higher than the frequency of operation of retarder 39. Filter 43 is preferably variable so that its cut-on or pass frequency can be varied. In one embodiment of FIG. 3, the high cut-on frequency was determined to be effective if set in the range from 100 KHZ to 2 MHZ, while the retarder was operating at only five to twelve cycles per second.

In the operation of the FIG. 3 embodiment, the user will watch monitor 45 while cycling retarder 39 with circuit 41. Light reflected from man-made objects will appear to flash as retarder 39 alternates between its rotated and nonrotated modes. Most natural objects in the background will not flash, because the reflected light from natural surfaces usually does not produce a strong polarizing contrast. The user adjusts notch filter 43 until much of the background is eliminated, but the flashing objects due to retarder 39 and polarizer 42 remain visible.

Figure 4:
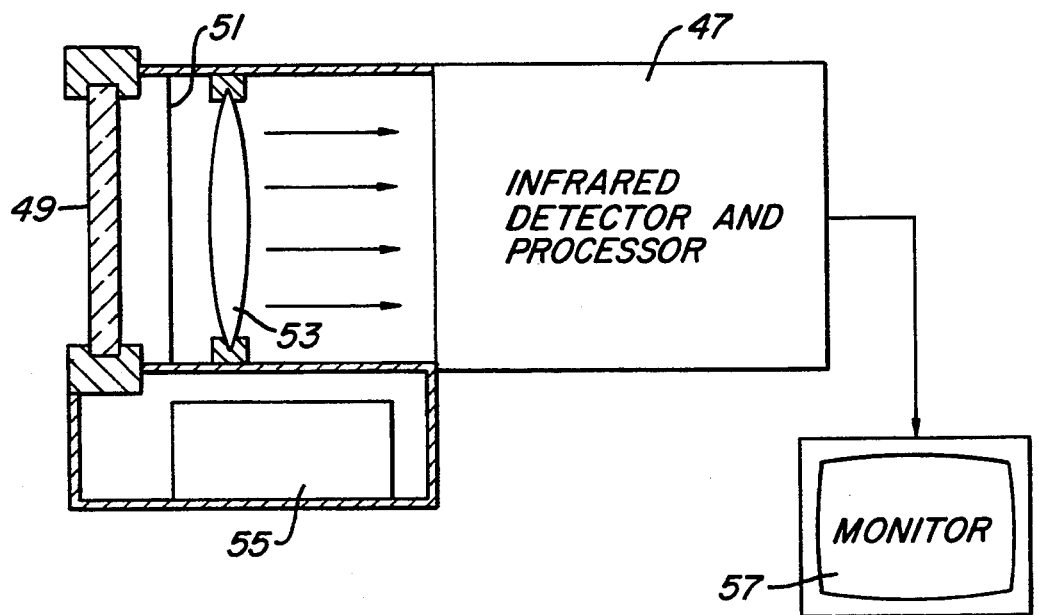
FIG. 4 is a schematic view illustrating an infrared detector having a polarizer and liquid crystal retarder mounted to it in accordance with this invention.

Referring to FIG. 4, in this embodiment, an infrared detector 47 is employed. Infrared detector 47 is of a conventional commercially available type. Liquid crystal retarder 49 is mounted in the image path of detector 47. The material of liquid crystal retarder 49 is selected for transmission of near infrared light in the range of 3 to 5 microns, or infrared light in the range of 8 to 14 microns. Polarizer 51 also is of the type that will transmit the same ranges of near infrared or infrared light. Polarizer 51 is stationarily located rearward of liquid crystal retarder 49. A lens 53 will focus light onto detector 47. A circuit 55 will alternately cycle liquid crystal retarder 49 between the rotated and nonrotated modes in the same manner as retarders 39 and 23 discussed above.

In the operation of the embodiment of FIG. 4, detector 47 processes and provides an image to a monitor 57. Detector 47 is preferably a forward-looking infrared detection device commercially available, and designed to operate in a 3 to 5 micron or 8 to 14 micron light range. Images detected by infrared detector 47 are polarized by polarizer 51. These images appear different to an observer depending on the mode of retarder 49, whether it is in the rotated or nonrotated mode. The differences can be visibly detected by an observer if the cycled speed of retarder 49 is slow enough.

Figure 2:
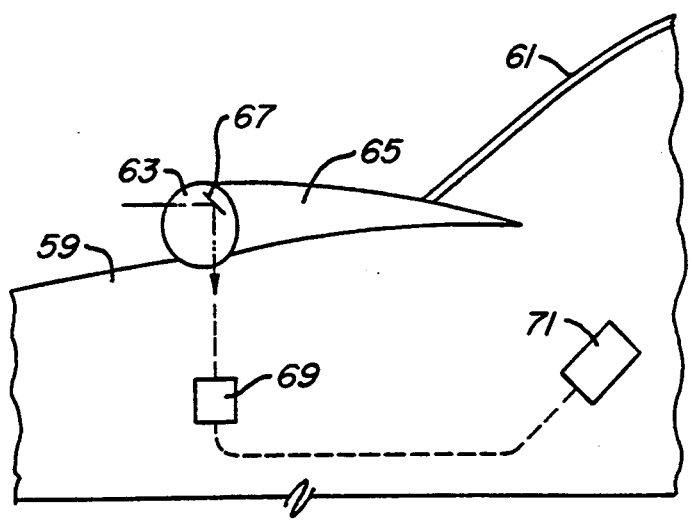
FIG. 2 is a side schematic view of a portion of an airplane having a detection system constructed in accordance with this invention.

FIG. 2 illustrates a portion of a fuselage 59 of an airplane. Fuselage 59 has a cockpit canopy 61. A transplant ball 63 rotatably mounts to fuselage 59. Ball 63 is mounted to a fairing 65. Ball 63 can be rotated for alignment and contains a focusing lens which focuses light onto a mirror 67. Mirror 67 reflects light down to a detection unit 69. Detection unit 69 provides a signal over wires to a monitor 71 located in the cockpit. Detection unit 69 may be either the infrared detector 47 (FIG. 4), the video camera 37 (FIG. 3) or some type of optical system utilizing the principle of binoculars 11.

The invention has significant advantages. It allows military target detection through camouflage and light foliage. The system can be mounted into an optical device such as binoculars, a video camera system, or an infrared detector. No moving components are required using the liquid crystal retarder. The stationary polarizer and liquid crystal retarder can be added without significant expense to existing binoculars, video surveillance or infrared detector systems. These systems can also be used in an ordinary manner if desired without the retarder being operated. The system can also be employed in helicopters to prevent pilots from colliding with power cables.

While the invention has been shown in only four of its forms, it should be apparent to those skilled in the art that it is not so limited but is susceptible to various changes without departing from the scope of the invention. For example, the invention could also be employed in night vision goggles.

I claim:

1. An apparatus for searching for selected objects, comprising in combination:
    a lens array defining an image path for viewing objects at which the apparatus is pointed;
    a light polarizer mounted to the apparatus in the image path which polarizes light received from objects and transmitted through the image path;
    a liquid crystal retarder means in the image path, including an electronic circuit and a liquid crystal retarder, for combining with the polarizer for alternately rotating light received from objects between a first angle of polarization and a second angle of polarization at a selected rate of oscillation, causing the images of certain of the objects viewed to appear to alternately flash.

2. The apparatus according to claim 1 wherein the polarizer is mounted to the apparatus rearward of the retarder means for polarizing light after the light has past through the retarder means.

3. The apparatus according to claim 1 wherein the retarder means rotates the light 90 degrees between the first and second angles of polarization.

4. The apparatus according to claim 1 wherein the retarder means comprises:
    a liquid crystal chamber mounted between a pair of glass surfaces and having a liquid crystal substance contained therein; and wherein the circuit alternately applies a first voltage between the glass surfaces to cause molecules in the liquid crystal substance to align with each other to cause the first angle of polarization, and when the voltage changes, to misalign with each other to cause the second angle of polarization.

5. The apparatus according to claim 1 wherein the rate at which the retarder means alternates is selectively variable.

6. The apparatus according to claim 1 wherein the rate at which the retarder means alternates is in the range of five to twelve cycles per second.

7. The apparatus according to claim 1 wherein the lens array comprises an optical array for receiving and passing visible light reflected from objects.

8. The apparatus according to claim 1 wherein the lens array is a video camera which electronically displays objects being observed.

9. The apparatus according to claim 1 wherein the lens array is an infrared detector which detects infrared radiation from objects being observed and displays objects observed in a form proportional to different wavelengths of infrared radiation being detected.

10. The apparatus according to claim 1, further comprising means for mounting the apparatus to a fuselage of an airplane.

11. The apparatus according to claim 1 wherein the lens array comprises video camera means for providing electrical signals for electronically displaying objects viewed; and wherein the apparatus further comprises:
frequency filter means for filtering electrical signals produced by the video camera means in a range below a selected frequency which is selected to substantially reduce the display of background objects viewed which reflect light that does not flash as the retarder means alternates.

12. The apparatus according to claim 1 wherein the polarizer is nonrotatably mounted to apparatus.

13. An apparatus for searching for selected objects, comprising in combination:
a lens array defining an image path for viewing objects at which the apparatus is pointed;
a liquid crystal retarder in the image path which when in a nonrotated mode passes light received from objects viewed substantially without effect, and when in a rotated mode, will rotate light 90 degrees received from objects viewed;
circuit means for alternately applying voltages to the retarder at a selected rate to cause the retarder to alternate between the rotated and nonrotated modes; and
a light polarizer mounted to the apparatus in the image path for polarizing light received from objects after passing through the retarder; and wherein
images of certain of the objects viewed will appear to alternately flash as the retarder is changed between the rotated and nonrotated modes.

14. The apparatus according to claim 13 whrein the rtarder comprises:
a liquid crystal chamber mounted between a pair of glass surfaces and having a liquid crystal substance contained therein.

15. The apparatus according to claim 13 wherein the rate at which the circuit means causes the retarder to alternate between the rotated mode and the nonrotated mode is selectively variable.

16. The apparatus according to claim 13 wherein the lens array comprises video camera means for providing electrical signals for electronically displaying objects viewed; and wherein the apparatus further comprises:
frequency filter means for filtering electrical signals in a range produced by the video camera means below a selected frequency which is selected to substantially reduce the display of background objects viewed which reflect light that does not differ whether the retarder is in the rotated mode or the nonrotated mode.

17. The apparatus according to claim 13 wherein the polarizer is stationarily mounted to apparatus.

18. An apparatus for searching for selected objects, comprising in combination:
lens array means for defining an image path for viewing objects at which the apparatus is pointed;
liquid crystal retarder means in the image path for passing light received from objects viewed substantially without effect when in a nonrotated mode, and when in a rotated mode, for rotating light 90 degrees received from objects viewed;
circuit means for alternately applying voltage to the retarder means at a selected variable rate to oscillate the retarder means between the rotated and nonrotated modes; and
light polarizer mounted stationarily to the apparatus in the image path for polarizing light received from objects after passing through the retarder means, so that images of objects viewed which will reflect light that will polarize will appear to alternately flash as the retarder means is oscillated between the rotated and nonrotated modes.

19. The apparatus according to claim 18 wherein the variable rate is in the range from five to twelve cycles per second.

20. A method for searching for selected objects, comprising in combination:
providing a lens array defining an image path and pointing the lens array at objects;
providing a liquid crystal retarder, and alternately rotating light in the image path received from objects between a rotated and a nonrotated mode; and
polarizing the light in the image path after passing through he retarder, and viewing the polarized light, the alternating modes of the retarder producing flashing of images of certain of the objects.

21. The method according to claim 20 wherein the step of alternately rotating light with the retarder comprises rotating the light 90 degrees.

22. The method according to claim 20 wherein the step of alternately rotating light with the retarder comprises rotating the light 90 degrees at a variable selected rate.

23. The method according to claim 20 wherein the step of polarizing the light comprises mounting a polarizer stationarily to a rearward side of the retarder.

24. The method according to claim 20 wherein the step of providing a lens array comprises providing a lens array which will pass visible light.

25. The method according to claim 20 wherein the step of providing a lens array comprises providing a lens array which will pass infrared light.

26. The method according to claim 20 wherein the step of providing a lens array comprises providing a video camera which provides electrical signals for electronically displaying objects viewed; and wherein the method further comprises:
filtering electrical signals produced by the video camera means in a range below a selected frequency which is selected to substantially reduce the display of background objects viewed which reflect light that does not differ whether the retarder is in the rotated mode or the nonrotated mode.

* * * * *